United States Patent
Reddy et al.

(10) Patent No.: US 8,178,680 B2
(45) Date of Patent: May 15, 2012

(54) PROCESS FOR THE PREPARATION OF MONTELUKAST AND ITS PHARMACEUTICALLY ACCEPTABLE SALTS

(75) Inventors: Manne Satyanarayana Reddy, Hyderabad (IN); Muppa Kishore Kumar, Hyderabad (IN); Srinivasan Thirumalai Rajan, Hyderabad (IN); Karamala Ramasubba Reddy, Kadapa (IN)

(73) Assignee: MSN Laboratories Limited, Andhra Pradesh, Hyderabad (IN)

( * ) Notice: Subject to any disclaimer, the term of this patent is extended or adjusted under 35 U.S.C. 154(b) by 777 days.

(21) Appl. No.: 12/086,436

(22) PCT Filed: Mar. 10, 2006

(86) PCT No.: PCT/IN2006/000086
§ 371 (c)(1),
(2), (4) Date: Jan. 30, 2009

(87) PCT Pub. No.: WO2007/069261
PCT Pub. Date: Jun. 21, 2007

(65) Prior Publication Data
US 2009/0171092 A1    Jul. 2, 2009

(30) Foreign Application Priority Data
Dec. 13, 2005  (IN) .......................... 1818/CHE/2005

(51) Int. Cl.
*C07D 215/18*    (2006.01)
(52) U.S. Cl. ...................................................... 546/174
(58) Field of Classification Search .................. None
See application file for complete search history.

(56) References Cited

U.S. PATENT DOCUMENTS

| | | | |
|---|---|---|---|
| 5,565,473 A | 10/1996 | Belley et al. | |
| 5,614,632 A | 3/1997 | Bhupathy et al. | |
| 2005/0107426 A1 | 5/2005 | Overeem et al. | |
| 2005/0107612 A1 | 5/2005 | Reguri et al. | |
| 2005/0234241 A1 | 10/2005 | Sundaram et al. | |
| 2006/0194838 A1 | 8/2006 | Chou et al. | |
| 2007/0078158 A1 | 4/2007 | Sterimbaum et al. | |
| 2010/0056793 A1 | 3/2010 | Reddy et al. | |

FOREIGN PATENT DOCUMENTS

| | | |
|---|---|---|
| EP | 0 480 717 B1 | 4/1998 |
| WO | WO 2004/108679 A1 | 12/2004 |
| WO | WO 2006/058545 A1 | 6/2006 |
| WO | WO 2007/004237 A2 | 1/2007 |
| WO | WO 2007/069261 | 6/2007 |
| WO | WO 2007/116240 A1 | 10/2007 |
| WO | WO 2008/062478 A2 | 5/2008 |

OTHER PUBLICATIONS

W.J. Kelly, Extraction Theory Presentation (2001), retrieved from the internet at: http://web.centre.edu/muzyka/organic/lab/24_extraction.htm.*
International Preliminary Examination Report for PCT/IN 2007/000542, Date of completion of report: Aug. 3, 2010, 14 pp.
Dufresne, C., et al., "Synthesis of Montelukast (MK-0476) Metabolic Oxidation Products," *J. Org. Chem.*, 61:8518-8525 (1996).
International Preliminary Examination Report for Int'l Application No. PCT/IN2006/000086, Date of Completion of Report: Jun. 13, 2008, 10 pages.
Written Opinion for PCT/IN2006/000086, Date Mailed: Sep. 25, 2006, 3 pages.
International Search Report for Int'l Application No. PCT/IN2007/000542, Date Mailed: Dec. 3, 2009.
International Search Report for Int'l Application No. PCT/IN2006/000086, Date Mailed: Sep. 25, 2006, 2 pages.
Written Opinion of the International Searching Authority for PCT/IN2007/00542 dated Dec. 3, 2009.
Notice of Allowance for U.S. Appl. No. 12/312,660 dated Dec. 15, 2011.

* cited by examiner

*Primary Examiner* — Janet Andres
*Assistant Examiner* — Timothy R Rozof
(74) *Attorney, Agent, or Firm* — Hamilton, Brook, Smith & Reynolds, P.C.

(57) ABSTRACT

An improved process for the preparation of Montelukast and its pharmaceutically acceptable salts comprises of reacting (S) Benzenepropanol α-[3-[2-(7-chloro2-quinolinyl)ethenyl]phenyl]-2-(1-hydroxy-1-methyl ethyl)-α-methane sulfonate compound of formula (II) with 1-(mercapto methyl) cyclo propane acetic acid or its ester or nitrile in presence of alkali or alkaline carbonates and/or alkali or alkaline earth metal alkoxide in a suitable polar aprotic solvent with or without combination of $C_1$-$C_4$ alcoholic solvents and then treating with organic amine in a suitable ester and/or acetone and/or aliphatic or aromatic hydrocarbon solvents, and converting the corresponding amine salt compound of montelukast into its sodium salt compound of formula (I) using sodium ion source in methanol, without converting into montelukast free acid.

(I)

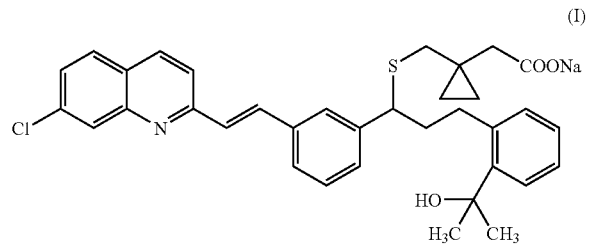

15 Claims, No Drawings

PROCESS FOR THE PREPARATION OF MONTELUKAST AND ITS PHARMACEUTICALLY ACCEPTABLE SALTS

RELATED APPLICATIONS

This application is the U.S. National Stage of International Application No. PCT/IN2006/000086, filed Mar. 10, 2006, published in English, and claims priority under 35 U.S.C. §365 to Indian Application No. 1818/CHE/2005, filed Dec. 13, 2005.

FIELD OF THE INVENTION

The present invention relates to an improved process for the preparation of [R-(E)-1[[[1-[3-[2-[7-chloro-2-quinolinyl] ethenyl]phenyl]-3-[2-(1-hydroxy-1-methylethyl)phenyl] propyl]thio]methyl]cyclopropaneacetic acid (Montelukast) and its pharmaceutically acceptable salts, preferably sodium salt. It can be represented as Formula (I).

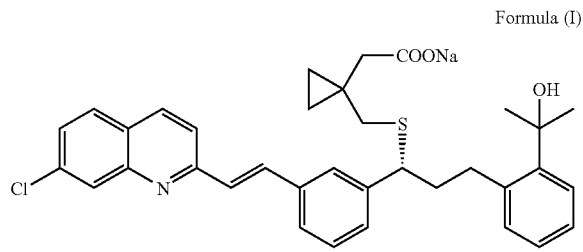

Formula (I)

Montelukast sodium is a leukotriene antagonist and is useful in the treatment of Asthma and as well as other conditions mediated by leukotrienes, such as inflammation and allergies.

BACKGROUND OF THE INVENTION

EP 480717 discloses certain substituted quinoline compounds including [R-(E)-1[[[1-[3-[2-[7-chloro-2-quinolinyl] ethenyl]phenyl]-3-[2-(1-hydroxy-1-methylethyl)phenyl] propyl]thio]methyl]cyclopropaneacetic acid sodium salt (Montelukast sodium salt), methods for their preparation and methods of pharmaceutical formulations using these compounds in mammals especially humans.

The process for the preparation comprises of reacting 2-(2-(2-(3(S)-(3-(2-(7-chloro-2-quinolinyl)ethenyl)phenyl)-3-(methanesulfonyloxy)propyl)phenyl)-2-propoxy)tetrahydro pyran with Methyl 1-(acetylthiomethyl)cyclopropane acetate in presence of hydrazine, cesium carbonate in acetonitrile as solvent to get methyl ester of Montelukast in pyran protected form. The protected compound is further reacted with pyridinium p-toluene sulfonate, sodium hydroxide in a mixture of methanol and tetrahydrofuran as a solvent to afford Montelukast sodium of Formula (I).

U.S. Pat. No. 5,614,632 discloses the preparation of 1-(mercapto methyl)cyclopropane acetic acid, which is a key intermediate for the preparation of Montelukast sodium. The said patent claimed an improved process for the preparation of Montelukast sodium including the process for the preparation of its key intermediates. The process comprises, the generation of dilithium dianion of 1-(mercaptomethyl)cyclopropaneacetic acid and then condensation with 2-(2-(2-(3(S)-(3-(2-(7-chloro-2-quinolinyl)ethenyl)phenyl)-3-(methane-sulfonyloxypropyl)phenyl)-2-propanol (referred as mesylated alcohol) to afford the Montelukast. It is further converted to its corresponding sodium salt via dicyclohexyl amine salt. The patent also discloses the process for the preparation of mesylated alcohol, which comprises reacting Methyl 2-(3(S)-(3-(2-(7-chloro-2-quinolinyl)ethenyl)phenyl)-3-hydroxy propyl)benzoate with methyl magnesium chloride to give diol, which is further converted to mesylated alcohol on reaction with methanol sulfonyl chloride. The process for the preparation of above described benzoate is disclosed in EP 480717 (example 146, step-2), which involves the usage of (−)B-chloro diisopinocamphenylborane as achiral reducing agent. The said patent also claims the process for the preparation of crystalline Montelukast sodium salt.

Many other related patents discloses the process for the preparation of Montelukast and its intermediates but none of those patents are related to the process of the present invention. The prior art procedures involves more number of steps which includes the protection and further deprotection of diol intermediate, the usage of hazardous and costly raw materials such as n-butyl lithium in typical reactions i.e., at very low temperatures (−25° C.). The processes of the prior art references involve tedious workup to isolate the required product and thus results in excess time cycle, which in turn rendering the process more costly and less eco friendly thus the process is not recommendable for commercial scale up.

As the Montelukast sodium of Formula (I), which is useful in the treatment of Asthma, hence, it is important to have a cost effective and commercially viable process for preparing the compound of Formula (I).

Therefore, the main objective of the present invention is to prepare Montelukast sodium in an improved method, which is cost-effective, commercially viable and non-hazardous. The Montelukast sodium is prepared in the present invention; in an improved process that is cost effective and the Montelukast sodium obtained in this process is suitable for pharmaceutical formulations.

DISADVANTAGES OF THE PRIOR ART PROCESSES

Usage of n-Butyl lithium is leading to increase the cost of the product and which is highly flammable and dangerous, it needs special equipment to handle the reagent, needs personal attention throughout the process.

Usage of sodium hydroxide for the preparation of Montelukast sodium (formula-I) from Montelukast produces water as by product it leads to formation of gummy material so removal of water is essential this leads to prolonged process.

Prior art processes teaches conversion of Montelukast amine salt to Montelukast free acid then converting to its sodium salt needs more time.

SUMMARY OF THE INVENTION

The present invention provides an improved process for the preparation of Montelukast and its pharmaceutically acceptable salts, preferably sodium salt. The improved process of the present invention comprises;

Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane acetic acid compound of formula (III) in presence of alkali or alkaline carbonates like cesium carbonate or strong base like alkali or alkaline earth metal alkoxide i.e., potassium tertiary butoxide, sodium methoxide, sodium ethoxide, in a suitable polar aprotic solvent with or without combination of C1-C4 alcoholic solvents like methanol, ethanol, preferably methanol and then treating with an organic amine of general formula R—NH$_2$ in a suitable solvent selected from keto solvents like acetone, butanone or ester solvents like ethyl acetate, propyl acetate, preferably acetone and ethylacetate gives corresponding amine salt of Montelukast compound of formula (IV) and then converting compound of corresponding amine salt of Montelukast into its sodium salt of Formula, (I) (Montelukast sodium) using sodium source in methanol.

ADVANTAGES OVER PRIOR ART PROCESSES

The object of the present invention is to provide an improved process for the preparation of Montelukast sodium using a simple base like sodium methoxide or potassium tertiary butoxide in place of n-butyl lithium which is easy to handle it does not need any special equipment.

Usage of sodium methoxide for the preparation of Montelukast sodium (formula-I) from Montelukast produces methanol as by product and removal of methanol is very easy and it gives the free flow powder.

Present invention provides process for the preparation of Montelukast sodium without conversion of Montelukast amine salt to Montelukast free acid, it leads to reduction of cycle time.

Highest yield obtained while using cesium carbonate.

Introducing the toluene/hexanes washings after completion of the condensation reaction to remove impurities, which avoids purification at organic amine salt stage.

Cost effective process, and reduction of cycle time.

Environment friendly and easy scalable process.

BRIEF DESCRIPTION OF THE INVENTION

The present invention provides an improved process for the preparation of Montelukast and its pharmaceutically acceptable salts, preferably sodium salt. The improved process of the present invention comprises the following steps;
1. Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane acetic acid compound of formula (III) in presence of polar aprotic solvent with or without combination of C1-C4 alcohol and strong base like alkali or alkaline earth metal alkoxides i.e., potassium tertiary butoxide, sodium methoxide, sodium ethoxide, preferably sodium methoxide in DMSO/Methanol.
2. Quenching the reaction mixture with water and adding sodium hydroxide and washing the reaction mixture with water immiscible solvents like hydrocarbon solvents, ester solvents, chloro solvents, preferably hydrocarbon solvents, more preferably toluene.
3. Lowering the pH of the reaction mixture by adding acetic acid to the reaction mixture and extracting the Montelukast with a suitable solvent selected from ester solvents, chloro solvents, preferably ester solvents, more preferably ethylacetate.
4. Treating the product obtained from step 3 with an organic amine compound of general formula R—NH$_2$ (wherein R is dicyclohexyl amine, tertiary butyl amine, isopropyl amine) in a suitable solvent selected from keto solvents like acetone, butanone or ester solvents like ethyl acetate, propyl acetate, preferably acetone and ethylacetate gives corresponding Montelukast amine salt compound of formula (IV).
5. Optionally purifying the corresponding amine salt of Montelukast using hydrocarbon solvents like toluene, hexanes, heptane or keto solvents like acetone or mixture of them.
6. Converting the Organic amine salt of Montelukast compound of formula (IV) into its sodium salt of Formula (I) using sodium source in methanol.

Another aspect of the present invention is to provide an improved process for the preparation of Montelukast sodium compound of formula (I) without converting the organic amine salt of Montelukast compound of formula (IV) to Montelukast free acid. Accordingly the present invention provides an improved process for the preparation of Montelukast sodium compound of formula (I) which comprises of following steps
a) Reacting the organic amine salt of Montelukast compound of formula (IV) with a sodium source in methanol.
b) Removing the organic amine by extracting the mass with solvents which are immiscible with methanol like hexanes, heptane, and concentrating the methanol.
c) Dissolving the product obtained from step b. in toluene and saturating the toluene with heptane to give Montelukast sodium compound of formula (I).

Another aspect of the present invention is to provide an improved process for the preparation of Montelukast sodium which comprises of following steps.
1. Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane methyl ester compound of formula (V) or 1-(mercapto methyl)cyclopropane acetonitrile compound of formula (VII) in presence of polar aprotic solvent with out combination of C1-C4 alcohol and strong base like alkali or alkaline earth metal alkoxides i.e., potassium tertiary butoxide, sodium methoxide, sodium ethoxide preferably sodium methoxide in DMSO/Methanol.
2. Optionally isolating the compound of formula (VI)/compound of formula (VIII) or in situ hydrolyzing with inorganic base like alkali metal hydroxide in a suitable solvent selected from hydrocarbon solvents, preferably toluene.
3. Treating the product obtained from step 2 with an organic amine compound of general formula R—NH$_2$ (wherein R is dicyclohexyl amine, tertiary butyl amine, isopropyl amine) in a suitable solvent selected from keto solvents like acetone, butanone or ester solvents like ethyl acetate, propyl acetate, preferably acetone and ethylacetate gives corresponding Montelukast amine salt compound of formula (IV).
4. Optionally purifying the corresponding amine salt of Montelukast using hydrocarbon solvents like toluene, hexanes, heptane or keto solvents like acetone or mixture of them.
5. Converting the Organic amine salt of Montelukast compound of formula (IV) into its sodium salt of Formula (I) using sodium source in methanol.

Yet another aspect of the present invention is to provide an improved process for the preparation of Montelukast sodium which comprises of the following steps;
1. Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane acetic acid compound of formula (III) or 1-(mercapto methyl)cyclopropane acetic acid methyl ester or 1-(mercapto methyl)cyclo propane acetonitrile in presence of polar aprotic solvent with or without combination of C1-C4 alcohol and alkali or alkaline carbonates like cesium carbonate, preferably cesium carbonate in presence of dimethylsulfoxide and methanol.

2. Quenching the reaction mixture with water and adding sodium hydroxide and washing the reaction mixture with water immiscible solvents like hydrocarbon solvents, ester solvents, chloro solvents, preferably hydrocarbon solvents, more preferably toluene.
3. Lowering the pH of the reaction mixture by adding acetic acid to the reaction mixture and extracting the Montelukast with a suitable solvent selected from ester solvents, chloro solvents, preferably ester solvents, more preferably ethylacetate.
4. Treating the product obtained from step 3 with an organic amine compound of general formula R—NH$_2$ (wherein R is dicyclohexyl amine, tertiary butyl amine, isopropyl amine) in a suitable solvent selected from keto solvents like acetone, butanone or ester solvents like ethyl acetate, propyl acetate, preferably acetone and ethylacetate gives corresponding Montelukast amine salt compound of formula (IV).
5. Optionally purifying the corresponding amine salt of Montelukast using hydrocarbon solvents like toluene, hexanes, heptanes or keto solvents like acetone or mixture of both.
6. Converting the Organic amine salt of Montelukast compound of formula (IV) into its sodium salt of Formula (I) using sodium source in methanol.

The present invention schematically represents as follows:

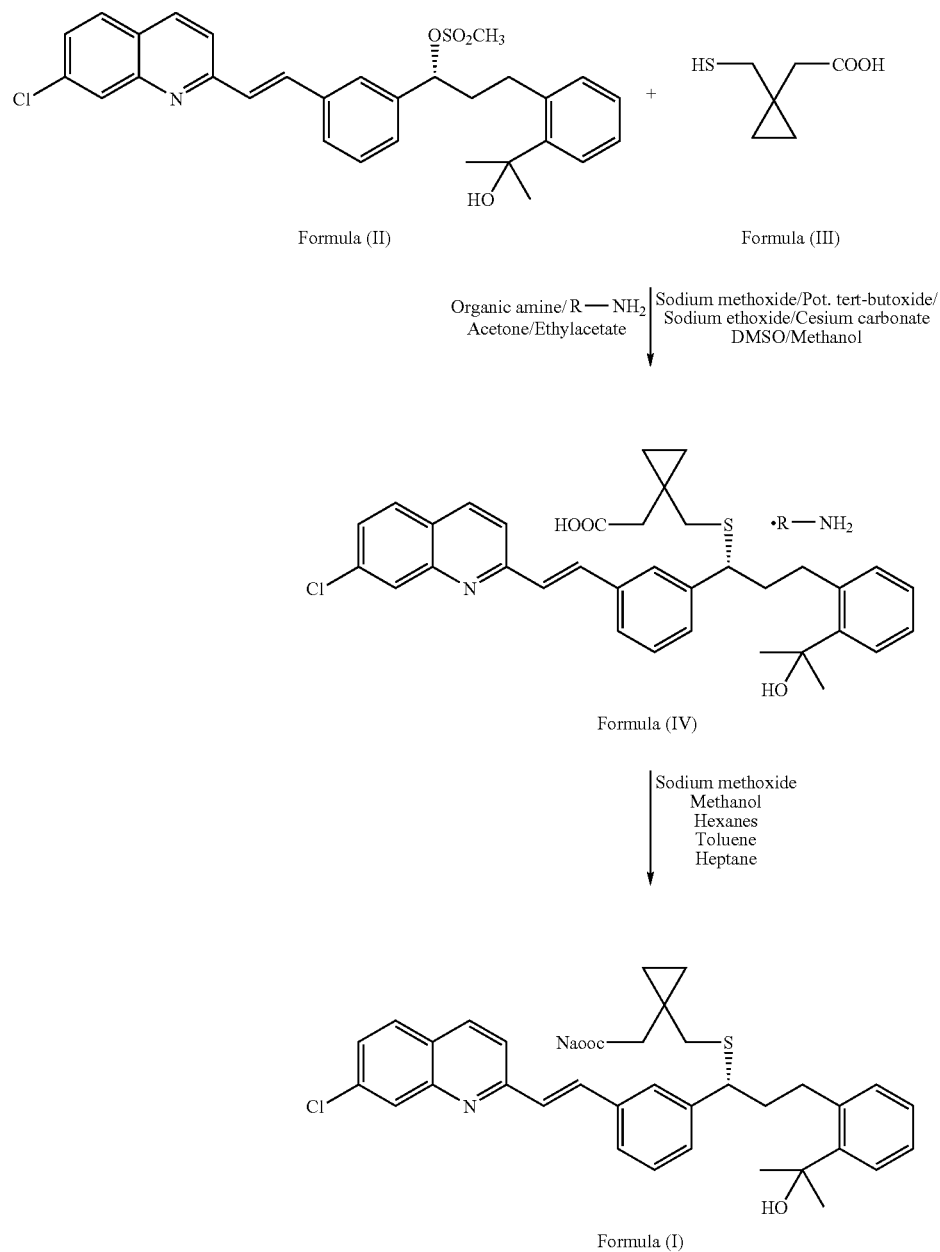

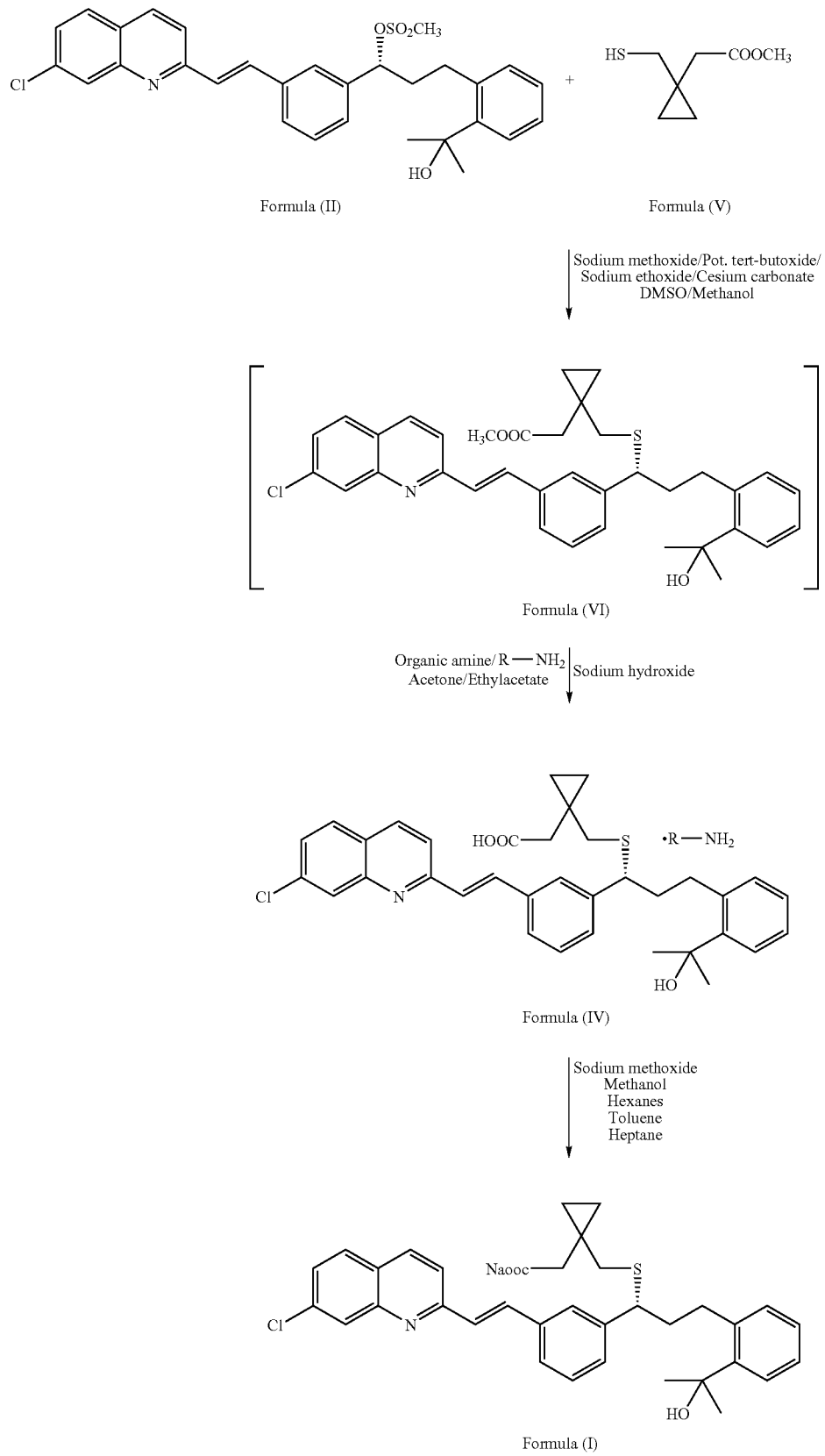

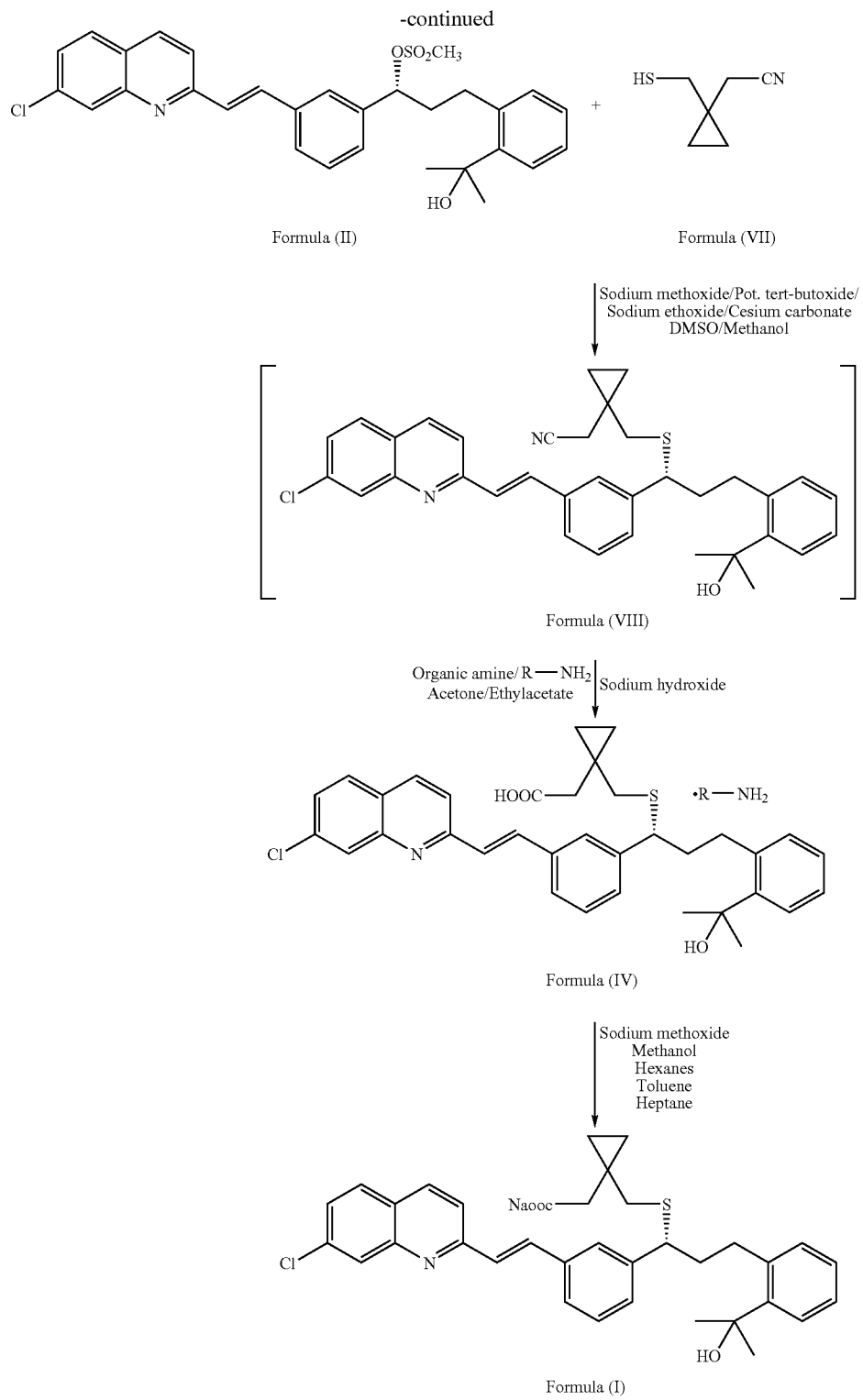

DETAILED DESCRIPTION OF THE PRESENT INVENTION

The present invention provides an improved process for the preparation of Montelukast and its pharmaceutically acceptable salts, preferably sodium salt. The improved process of the present invention comprises of;

a) Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane acetic acid compound of formula (III) in presence of polar aprotic solvents like dimethylsulfoxide, dimethyl acetamide with or without combination of C1-C4 alcoholic solvents like methanol, ethanol, propanol, butanol, and strong base like alkali or alkaline earth metal alkoxides i.e., potassium tertiary butoxide, sodium methoxide, sodium ethoxide, preferably sodium methoxide in a mixture of methanol and DMSO (dimethylsulfoxide) at a temperature of −20 to 0° C. for 5 to 20 hours, preferably at a temperature of about −5 to 5° C. for 8-10 hours.

b) Quenching the reaction mixture with water and adding sodium hydroxide solution to the reaction mixture, and then extracting with water immiscible solvents like hydrocarbon solvents, chloro solvents, ester solvents, preferably hydrocarbon solvents more preferably toluene.

c) Lowering pH of the reaction mixture with acetic acid then extracting the Montelukast with ester solvents, chloro solvents, preferably ester solvents more preferably ethylacetate. Concentrating the solvent and diluting with a suitable solvent selected from keto solvents like acetone, butanone or ester solvents like ethylacetate, propyl acetate, preferably acetone and ethylacetate.

d) Treating the product obtained from step c. with an organic amine having general formula R—NH$_2$ (i.e., organic amine like cyclic amines such as cyclopropyl amine, cyclo pentyl amine, cyclo hexyl amine, dicyclohexyl amine, pyrrolidine or morpholine or alkyl amines such as methyl amine, isopropyl amine, diisopropyl amine, tert-butyl amine, n-octyl glucamine or aryl amines such as phenyl ethyl amine, phenyl propyl amine) in a suitable solvent selected from keto solvents like acetone, butanone or ester solvents like ethyl acetate, propyl acetate, preferably acetone and ethylacetate at a temperature of 20-40° C. for 5-15 hours, preferably at a temperature of about 25-35° C. for 8-10 hours under inert atmosphere to give a respective salt of compound of formula (IV).

e) Optionally purifying the corresponding amine salt of Montelukast using hydrocarbon solvents like toluene, hexanes, heptane or keto solvents like acetone or mixture of them.

f) Converting the Organic amine salt of Montelukast compound of formula (IV) into its sodium salt of Formula (I) using sodium methoxide in methanol using sodium methoxide in methanol at a temperature of 20-40° C. for 1-2 hours, preferably at a temperature of 25-35° C. for 45 minutes under inert atmosphere.

Another aspect of the present invention is to provide an improved process for the preparation of Montelukast sodium compound of formula (I) which comprises the following steps a) Reacting the organic amine salt of Montelukast compound of formula (IV) with a sodium source like sodium methoxide or sodium hydroxide in methanol.

b) Removing the organic amine by extracting the mass with solvents which are immiscible with methanol like hexanes, heptane, and concentrating the methanol.

c) Dissolving the product obtained from step b. in toluene and saturating the toluene with heptane to give Montelukast sodium compound of formula (I).

Another aspect of the present invention is to provide an improved process for the preparation of Montelukast sodium compound of formula (I) which comprises the following steps.

1. Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-mercapto methyl cyclopropane methyl ester compound of formula (V) or 1-mercapto methyl cyclopropane acetonitrile compound of formula (VII) in presence of polar aprotic solvent like dimethylsulfoxide, dimethyl acetamide with or without combination of C1-C4 alcoholic solvents like methanol, ethanol, propanol, butanol, and strong base like alkali or alkaline earth metal alkoxides i.e., potassium tertiary butoxide, sodium methoxide, sodium ethoxide, preferably sodium methoxide in a mixture of methanol and DMSO (dimethylsulfoxide) at a temperature of −20 to 0° C. for 5 to 20 hours, preferably at a temperature of about −5 to 5° C. for 8-10 hours.

2. Optionally isolating the compounds of formula (VI)/compound of formula (VIII) or in situ hydrolyzing with inorganic base like alkali metal hydroxide in a suitable solvent selected from hydrocarbon solvents like toluene, xylene, preferably toluene at a temperature of 10-70° C. for 10-20 hours, preferably at a temperature of 40-50° C. for 15 hours.

3. Treating the product obtained from step 2 with an organic amine compound of general formula R—NH$_2$ (wherein R is dicyclohexyl amine, tertiary butyl amine, isopropyl amine) in a suitable solvent selected from keto solvents like acetone, butanone or ester solvents like ethyl acetate, propyl acetate, preferably acetone and ethylacetate at a temperature of 20-40° C. for 5-15 hours, preferably at a temperature of about 25-35° C. for 8-10 hours under inert atmosphere to give a respective salt of compound of formula (IV).

4. Optionally purifying the corresponding amine salt of Montelukast using hydrocarbon solvents like toluene, hexanes, heptane or keto solvents like acetone or mixture of them.

5. Converting the Organic amine salt of Montelukast compound of formula (IV) into its sodium salt of Formula (I) using sodium methoxide in methanol at a temperature of 20-40° C. for 1-2 hours, preferably at a temperature of 25-35° C. for 60 minutes under inert atmosphere.

Yet another aspect of the present invention is to provide an improved process for the preparation of Montelukast sodium which comprises of the following steps;

1. Reacting (S) Benzenepropanol α-[3-[2-(7-chloro-2-quinolinyl)ethenyl]phenyl]-2-(1-hydroxy-1-methyl ethyl)-α-methane sulfonate compound of formula (II) with 1-(mercapto methyl)cyclopropane acetic acid compound of formula (III) or 1-(mercapto methyl)cyclopropane acetic acid methyl ester or 1-(mercapto methyl)cyclo propane acetonitrile in presence of polar aprotic solvent like dimethyl sulfoxide, dimethyl acetamide with or without combination of C1-C4 alcohol and alkali or alkaline carbonates like cesium carbonate at a temperature of −20 to 0° C. for 5 to 20 hours, preferably at a temperature of about −5 to 5° C. for 8-10 hours.

2. Quenching the reaction mixture with water and adding sodium hydroxide and washing the reaction mixture with water immiscible solvents like hydrocarbon solvents, ester solvents, chloro solvents, preferably hydrocarbon solvents, more preferably toluene.

3. Lowering the pH of the reaction mixture by adding acetic acid to the reaction mixture and extracting the Montelukast with a suitable solvent selected from ester solvents, chloro solvents, preferably ester solvents, more preferably ethylacetate.

4. Treating the product obtained from step 3 with an organic amine compound of general formula R—NH$_2$ (wherein R is dicyclohexyl amine, tertiary butyl amine, isopropyl amine) in a suitable solvent selected from keto solvents like acetone, butanone or ester solvents like ethyl acetate, propyl acetate, preferably acetone and ethylacetate at a temperature of 20-40° C. for 5-15 hours, preferably at a temperature of about 25-35° C. for 8-10 hours under inert atmosphere to give a respective salt of compound of formula (IV).

5. Optionally purifying the corresponding amine salt of Montelukast using hydrocarbon solvents like toluene, hexanes, heptane or keto solvents like acetone or mixture of them.
6. Converting the Organic amine salt of Montelukast compound of formula (IV) into its sodium salt of Formula (I) using sodium methoxide in methanol at a temperature of 20-40° C. for 1-2 hours, preferably at a temperature of 25-35° C. for 60 minutes under inert atmosphere.

The processes described in the present invention were demonstrated in examples illustrated below. These examples are provided as illustration only and therefore should not be construed as limitation of the scope of the invention.

EXAMPLES

Example-1

Preparation of Dicyclohexyl Amine Salt of [R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and sodium methoxide solution (200 ml) in methanol is cooled to −5 to 0° C. under nitrogen atmosphere. Added 1-(mercapto methyl) cyclo propane acetic acid (35 gr) compound of formula (III) under nitrogen atmosphere. Stirred the reaction mixture for 60 minutes at −5 to 0° C. Added 100 gr of (S) Benzenepropanol α-[3-[2-(7-chloro-2-quinolinyl)ethenyl]phenyl]-2-(1-hydroxy-1-methyl ethyl)-α-methane sulfonate compound of formula (II) to the reaction mixture at −5-0° C. Stirred the reaction mixture at −5 to 5° C. for 10 hours. Added the reaction mixture to 3000 ml of chilled Water. Stirred the reaction mixture at 10-20° C. for 30 minutes. Slowly added sodium hydroxide solution at 10-20° C. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of ethylacetate to the above obtained crude at 25-35° C. and stirred for 45 minutes under nitrogen atmosphere. Added 55 ml of dicyclohexylamine at 25-35° C. Stirred the reaction mixture for 10 hours. Filtered the solid and washed with ethylacetate under nitrogen atmosphere. Wet material taken into a mixture of 500 ml of toluene and 500 ml of hexenes and heated to 55-65° C., stirred for 60 minutes. Cooled the mass to 25-35° C. and stirred for 8 hours. Separated the solid by filtration. Dried the compound at 40-60° C. to get title compound. Yield: 80 gr.

Example-2

Preparation of Dicyclohexyl Amine Salt of [R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and sodium methoxide solution (200 ml) in methanol is cooled to −5 to 0° C. under nitrogen atmosphere. Added 1-(mercapto methyl) cyclo propane acetic acid (35 gr) compound of formula (III) under nitrogen atmosphere. Stirred the reaction mixture for 60 minutes at −5 to 0° C. Added 100 gr of (S) Benzenepropanol α-[3-[2-(7-chloro-2-quinolinyl)ethenyl]phenyl]-2-(1-hydroxy-1-methyl ethyl)-α-methane sulfonate compound of formula (II) to the reaction mixture at −5-0° C. Stirred the reaction mixture at −5 to 5° C. for 10 hours. Added the reaction mixture to 3000 ml of chilled Water. Stirred the reaction mixture at 10-20° C. for 30 minutes. Slowly added sodium hydroxide solution at 10-20° C. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of acetone to the above obtained crude at 25-35° C. and stirred for 45 minutes under nitrogen atmosphere. Added 55 ml of dicyclohexylamine at 25-35° C. Stirred the reaction mixture for 10 hours. Filtered the solid and washed with acetone under nitrogen atmosphere. Dried the compound at 40-60° C. to get title compound. Yield: 80 gr.

Example-3

Preparation of Tertiary Butyl Amine Salt of [R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and sodium methoxide solution (200 ml) in methanol is cooled to −5 to 0° C. under nitrogen atmosphere. Added 1-(mercapto methyl) cyclo propane acetic acid (35 gr) compound of formula (III) under nitrogen atmosphere. Stirred the reaction mixture for 60 minutes at −5 to 0° C. Added 100 gr of (S) Benzenepropanol α-[3-[2-(7-chloro-2-quinolinyl)ethenyl]phenyl]-2-(1-hydroxy-1-methyl ethyl)-α-methane.sulfonate compound of formula (II) to the reaction mixture at −5-0° C. Stirred the reaction mixture at −5 to 5° C. for 10 hours. Added the reaction mixture to 3000 ml of chilled Water. Stirred the reaction mixture at 10-20° C. for 30 minutes. Slowly added sodium hydroxide solution at 10-20° C. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of acetone to the above obtained crude at 25-35° C. and stirred for 45 minutes under nitrogen atmosphere. Added 15 gr of tertiary butyl amine at 25-35° C. Stirred the reaction mixture for 10 hours. Filtered the solid and washed with acetone under nitrogen atmosphere. Dried the compound at 40-60° C. to get title compound. Yield: 70 gr.

Examples-4

Preparation of Dicyclohexyl Amine Salt of [R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and sodium methoxide solution (200 ml) in methanol is cooled to −5 to 0° C. under nitrogen atmosphere. Added 1-(mercapto methyl) cyclo propane acetic acid methyl ester compound of formula (V) (45 gr) compound of formula (III) under nitrogen atmosphere. Stirred the reaction mixture for 60 minutes at −5 to 0° C. Added 100 gr of (S) Benzenepropanol α-[3-[2-(7-chloro-2-quinolinyl)ethenyl]phenyl]-2-(1-hydroxy-1-methyl ethyl)-

α-methane sulfonate compound of formula (II) in DMSO (dimethyl sulfoxide) to the reaction mixture at −5-0° C. Stirred the reaction mixture at −5 to 5° C. for 10 hours. Added the reaction mixture to 1000 ml of chilled Water. Stirred the reaction mixture at 10-20° C. for 30 minutes. Extracted the reaction mixture with toluene. Concentrated the toluene layer completely and added toluene to the residue. Added sodium hydroxide solution and stirred at a temperature of about 40 to 50° C. for 15 hours. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of acetone to the above obtained crude at 25-35° C. and stirred for 45 minutes under nitrogen atmosphere. Added 55 ml of dicyclohexylamine at 25-35° C. Stirred the reaction mixture for 10 hours. Filtered the solid and washed with acetone under nitrogen atmosphere. Dried the compound at 40-60° C. to get title compound. Yield: 80 gr.

Example-5

Preparation of Dicyclohexyl Amine Salt of [R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and sodium methoxide solution (200 ml) in methanol is cooled to −5 to 0° C. under nitrogen atmosphere. Added 1-(mercapto methyl) cyclo propane acetonitrile compound of formula (VII) (25 gr) compound of formula (III) under nitrogen atmosphere. Stirred the reaction mixture for 60 minutes at −5 to 0° C. Added 100 gr of (S) Benzenepropanol α-[3-[2-(7-chloro-2-quinolinyl)ethenyl]phenyl]-2-(1-hydroxy-1-methyl ethyl)-α-methane sulfonate compound of formula (II) in DMSO (dimethyl sulfoxide) to the reaction mixture at −5-0° C. Stirred the reaction mixture at −5 to 5° C. for 10 hours. Added the reaction mixture to 1000 ml of chilled Water. Stirred the reaction mixture at 10-20° C. for 30 minutes. Extracted the reaction mixture with toluene. Concentrated the toluene layer completely and added toluene to the residue. Added caustic lye solution and stirred at a temperature of 125° C. for 15 hours. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of acetone to the above obtained crude at 25-35° C. and stirred for 45 minutes under nitrogen atmosphere. Added 55 ml of dicyclohexylamine at 25-35° C. Stirred the reaction mixture for 10 hours. Filtered the solid and washed with acetone under nitrogen atmosphere. Dried the compound at 40-60° C. to get title compound. Yield: 65 gr.

Example-6

Preparation of Dicyclohexyl Amine Salt of R-(E)-1 [[[1-[3-[2-[7-chloro-2-quinolinyl]ethenyl]phenyl]-3-[2-(1-hydroxy-1-methylethyl)phenyl]propyl]thio] methyl]cyclopropaneacetic Acid Compound of Formula (IV)

A solution of dimethylsulfoxide (400 ml) and cesium carbonate (120 gr) in methanol (200 ml) is cooled to −5 to 0° C. under nitrogen atmosphere. Added 1-(mercapto methyl)cyclo propane acetic acid (35 gr) compound of formula (III) under nitrogen atmosphere. Stirred the reaction mixture for 60 minutes at −5 to 0° C. Added 100 gr of (S) Benzenepropanol, α-[3-[2-(7-chloro-2-quinolinyl)ethenyl]phenyl]-2-(1-hydroxy-1-methyl ethyl)-, α-methane sulfonate compound of formula (II) to the reaction mixture at −5-0° C. Stirred the reaction mixture at −5 to 5° C. for 10 hours. Added the reaction mixture to 3000 ml of chilled Water. Stirred the reaction mixture at 10-20° C. for 30 minutes. Slowly added sodium hydroxide solution at 10-20° C. Washed the reaction mixture with toluene and removed the toluene layer. Cooled the aqueous layer to 10-20° C. and slowly added 50% acetic acid solution. Extracted the reaction mixture with ethylacetate, washed the total organic layer with water and concentrated the organic layer at below 55° C. under reduced pressure. Added 500 ml of acetone to the above obtained crude at 25-35° C. and stirred for 45 minutes under nitrogen atmosphere. Added 55 ml of dicyclohexylamine at 25-35° C. Stirred the reaction mixture for 10 hours. Filtered the solid and washed with acetone under nitrogen atmosphere. Dried the compound at 40-60° C. to get title compound. Yield: 100 gr.

Example-7

Preparation of Sodium Salt of [R-(E)-1[[[1-[3-[2-[7-chloro-2-quinolinyl]ethenyl]phenyl]-3-[2-(1-hydroxy-1-methylethyl)phenyl]propyl]thio]methyl] cyclopropaneacetic Acid Compound of Formula (I)

Added dicyclohexyl amine salt of [R-(E)-1[[[1-[3-[2-[7-chloro-2-quinolinyl]ethenyl]phenyl]-3-[2-(1-hydroxy-1-methylethyl)phenyl]propyl]thio]methyl]cyclopropaneacetic acid compound of formula (IV) (100 gr) prepared as per the procedures given in examples 1, 2, 4, 5 & 6 to a solution of sodium methoxide (23 gr) and methanol (210 ml) at 25-35° C. Stirred for 60 minutes at 25-35° C. Washed the reaction mixture with hexanes. Distilled the solvent completely under reduced pressure at below 55° C. Added toluene to the crude and slowly added the toluene layer to heptane at 25-35° C. under nitrogen atmosphere. Stirred the mass for 45 minutes under nitrogen atmosphere. Separated the solid by filtration and washed with heptane. Dried the compound at 60-70° C. under reduced pressure to get title compound. Yield 70 gr.

Example-8

Preparation of Sodium Salt of [R-(E)-1[[[1-[3-[2-[7-chloro-2-quinolinyl]ethenyl]phenyl]-3-[2-(1-hydroxy-1-methylethyl)phenyl]propyl]thio]methyl] cyclopropaneacetic Acid Compound of Formula (I)

Added tertiary butyl amine salt of [R-(E)-1[[[1-[3-[2-[7-chloro-2-quinolinyl]ethenyl]phenyl]-3-[2-(1-hydroxy-1-methylethyl)phenyl]propyl]thio]methyl]cyclopropaneacetic acid compound of formula (IV) (100 gr) prepared as per the procedures given in examples 3, to a solution of sodium methoxide (22 gr) and methanol (210 ml) at 25-35° C. Stirred for 60 minutes at 25-35° C. Washed the reaction mixture with hexanes. Distilled the solvent completely under reduced pressure at below 55° C. Added toluene to the crude and slowly added the toluene layer to heptane at 25-35° C. under nitrogen atmosphere. Stirred the mass for 45 minutes under nitrogen atmosphere. Separated the solid by filtration and washed with heptane. Dried the compound at 60-70° C. under reduced pressure to get title compound. Yield 70 gr.

We claim:

1. A method for the preparation of a compound of formula (I)

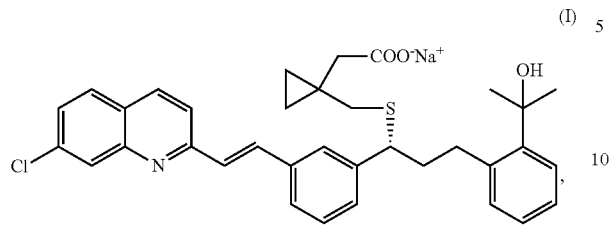

comprising:
(a) reacting a compound of formula (II)

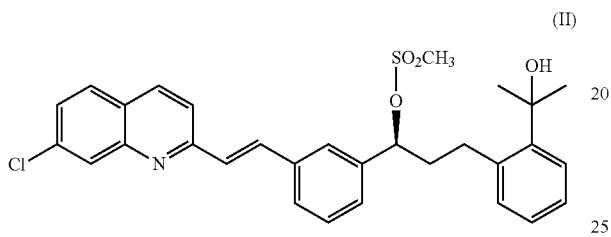

with a compound of formula (III)

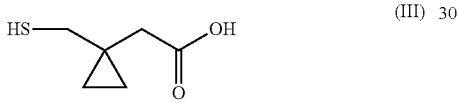

in the presence of a polar aprotic solvent and a base at a temperature of −20 to 0° C. for 5 to 20 hours;
(b) quenching the reaction mixture with water and sodium hydroxide;
(c) extracting the reaction mixture obtained in step (b) with a water-immiscible solvent, thereby removing impurities from the reaction mixture;
(d) adding acetic acid to the reaction mixture obtained in step (c), thereby lowering pH of the reaction mixture;
(e) extracting the product obtained in step (d) with a solvent selected from an ester solvent and a chloro solvent;
(f) concentrating the reaction mixture obtained in step (e);
(g) diluting the reaction mixture obtained in step (f) with a solvent selected from a keto solvent or an ester solvent;
(h) treating the product obtained from step (g) with an amine of formula (R)$_2$—NH at a temperature of 20-40° C. for 5-15 hours under inert atmosphere to produce a compound of formula (IVa)

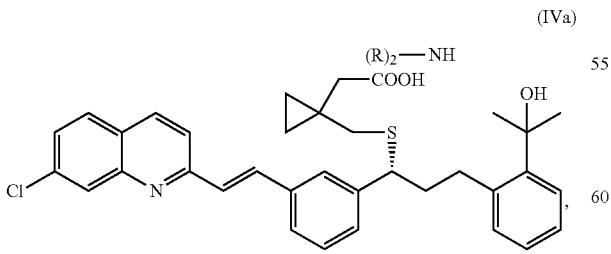

wherein each R is independently hydrogen, a C1-C12 alkyl, a C2-C12 heteroaryl, a C3-C8 cycloalkyl, a 3 to 8-membered heterocycloalkyl, a C6-C18 aryl, or a C6-C18 heteroaryl, or wherein two R groups taken together with their intervening nitrogen atom form a 3- to 8-membered optionally substituted non-aromatic heterocycle;
(i) optionally, purifying the compound of formula (IVa) obtained in step (h) using a hydrocarbon solvent, a keto solvent or a mixture thereof; and
(j) reacting the product of step (h) or step (i) with sodium methoxide in methanol at a temperature of 20-40° C. for 1-2 hours, thereby converting the compound of formula (IVa) into the compound of formula (I) without converting the compound of formula (IVa) to montelukast free acid.

2. The method of claim 1, wherein the polar aprotic solvent used in step (a) is dimethyl sulfoxide or dimethylacetamide, and the base used in step (a) is an alkali or alkaline earth metal alkoxide.

3. The method of claim 1, wherein the water-immiscible solvent used in step (c) is toluene.

4. The method of claim 1, wherein the water-immiscible solvent used in step (c) is heptane.

5. A method for the preparation of a compound of formula (I),

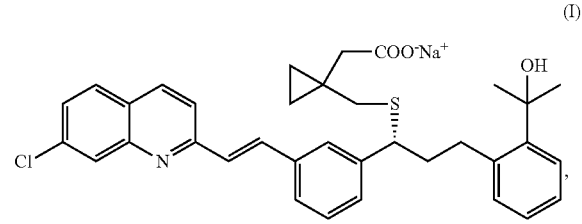

the method comprising:
(a) reacting an organic amine salt of the compound of formula (IVa)

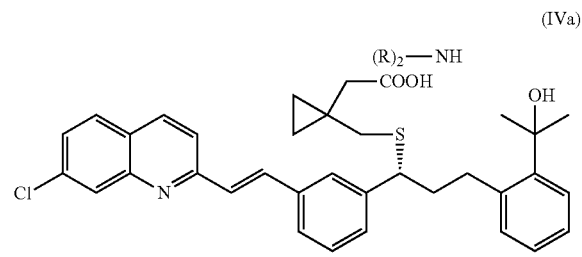

with a sodium ion source in methanol, provided that an acid source is not used for in situ generation of a free acid of the compound of formula (IVa), thereby obtaining the compound of formula (I) without converting the compound of formula (IVa) to the free acid of the compound of formula (IVa),
wherein each R is independently hydrogen, a C1-C12 alkyl, a C2-C12 heteroaryl, a C3-C8 cycloalkyl, a 3 to 8-membered heterocycloalkyl, a C6-C18 aryl, or a C6-C18 heteroaryl, or
wherein two R groups taken together with their intervening nitrogen atom form a 3- to 8-membered optionally substituted non-aromatic heterocycle;
(b) optionally, removing the organic amine by washing the reaction mixture obtained in step (a) with a methanol-immiscible solvent, thereby obtaining a methanol layer containing the compound of formula (I) and a methanol-immiscible solvent layer containing the organic amine, and removing the methanol-immiscible solvent layer containing the organic amine;

(c) concentrating the methanol layer containing the compound of formula (I); and (d) dissolving the product of step (c) in toluene and saturating the toluene solution with heptane.

6. The method of claim 5, wherein the sodium ion source used in step (a) is sodium methoxide.

7. The method of claim 5, wherein the methanol-immiscible solvent used in step (b) is hexanes.

8. A method for the preparation of a compound of formula (I)

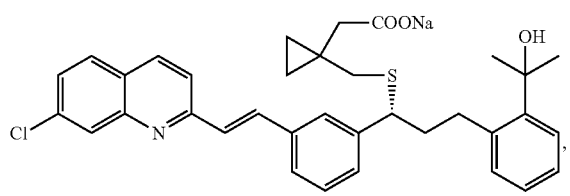

the method comprising:

(a) reacting a compound of formula (II)

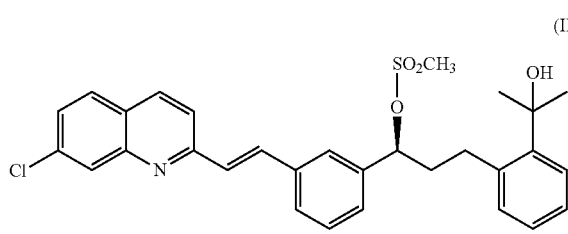

with a compound of formula (V)

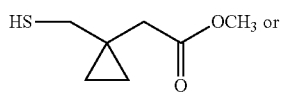

a compound of formula (VII)

in the presence of a polar aprotic solvent and a base at a temperature of −20 to 0° C. for 5 to 20 hours, thereby producing a compound of formula (VI) or (VIII), respectively

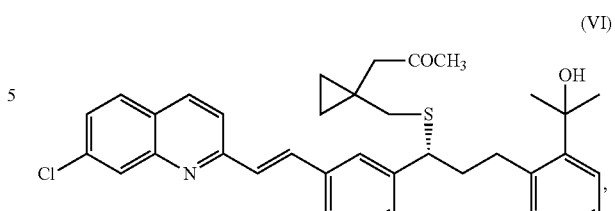

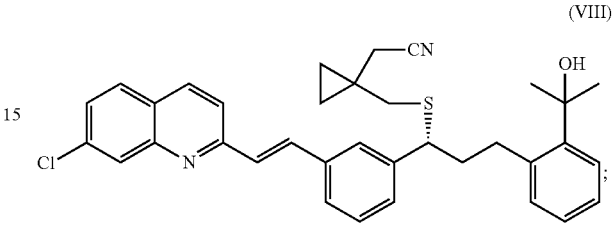

(b) optionally, isolating the compound of formula (VI) or the compound of formula (VIII);

(c) hydrolyzing, optionally in situ, the compound of formula (VI) or (VIII) with an inorganic base in a C1-C4 alcohol at a temperature of 10-70° C. for 10-20 hours;

(d) treating the product obtained from step (c) with a primary or secondary organic amine in a keto solvent or an ester solvent at a temperature of 20-40° C. for 5-15 hours, thereby producing a compound of formula (IVa)

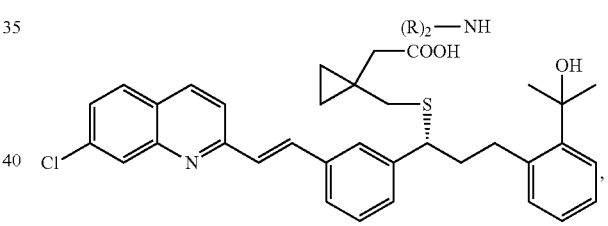

wherein each R is independently hydrogen, a C1-C12 alkyl, a C2-C12 heteroaryl, a C3-C8 cycloalkyl, a 3 to 8-membered heterocycloalkyl, a C6-C18 aryl, or a C6-C18 heteroaryl, or wherein two R groups taken together with their intervening nitrogen atom form a 3- to 8-membered optionally substituted non-aromatic heterocycle;

(e) optionally, purifying the compound of formula (IVa) obtained in step (d) using a hydrocarbon solvent or a mixture thereof;

(f) treating the compound of formula (IVa) obtained in step (d) or (e) with sodium methoxide in methanol at a temperature of 20-40° C. for 1-2 hours under inert atmosphere, thereby converting the compound of formula (IVa) into the compound of formula (I) without converting the compound of formula (IVa) to montelukast free acid.

9. The method of claim 8, wherein the polar aprotic solvent used in step (a) is dimethyl sulfoxide or dimethylacetamide, and the base used in step (a) is an alkali or alkaline earth metal alkoxide.

10. A method for the preparation of a compound of formula (I)

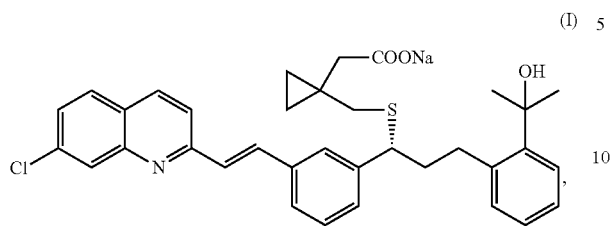

the method comprising:
(a) reacting a compound of formula (II)

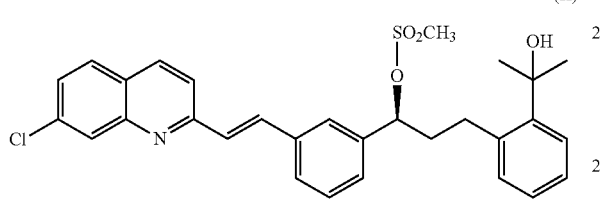

with a compound of formula (III)

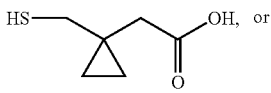

a compound of formula (V)

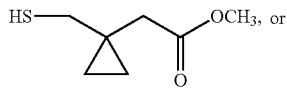

a compound of formula (VII)

in the presence of a polar aprotic solvent and a base at a temperature of −20 to 0° C. for 5 to 20 hours;
(b) quenching the reaction mixture of step (a) with water and sodium hydroxide;
(c) extracting the reaction mixture of step (b) with a water-immiscible solvent, thereby removing impurities from the reaction mixture;
(d) adding acetic acid to the reaction mixture of step (c), thereby lowering pH of the reaction mixture;
(e) extracting the reaction product of step (d) with an ester solvent;
(f) concentrating the product extracted in step (e);
(g) diluting the product of step (f) with a keto solvent or an ester solvent;
(h) treating the product obtained from step (g) with a primary or secondary organic amine in a keto solvent or an ester solvent at a temperature of 20-40° C. for 5-15 hours under inert atmosphere, thereby producing a compound of formula (IVa)

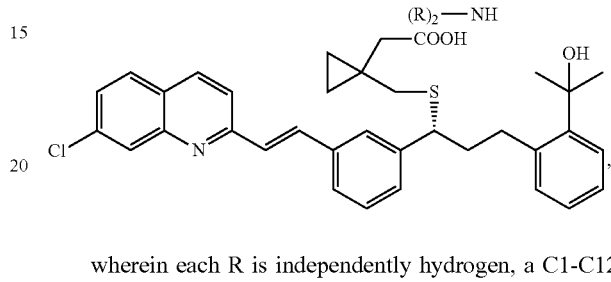

wherein each R is independently hydrogen, a C1-C12 alkyl, a C2-C12 heteroaryl, a C3-C8 cycloalkyl, a 3 to 8-membered heterocycloalkyl, a C6-C18 aryl, or a C6-C18 heteroaryl, or
wherein two R groups taken together with their intervening nitrogen atom form a 3- to 8-membered optionally substituted non-aromatic heterocycle;
(i) optionally, purifying the compound of formula (IVa) by extracting the compound of formula (IVa) with a hydrocarbon solvent or a mixture of thereof;
(j) treating the compound of formula (IVa) obtained in step (h) or step (i) with sodium methoxide in methanol at a temperature of 20-40° C. for 1-2 hours under inert atmosphere, thereby converting the compound of formula (IVa) into the compound of formula (I) without converting the compound of formula (IVa) to montelukast free acid.

11. The method of claim 10, wherein the polar aprotic solvent used in step (a) is dimethyl sulfoxide or dimethyl acetamide and wherein the base used in step (a) is an alkaline carbonate.

12. The method of claim 11, wherein the alkaline carbonate used in step (a) is cesium carbonate.

13. The method of claim 10, wherein the polar aprotic solvent used in step (a) is dimethyl sulfoxide or dimethylacetamide, optionally in combination with a C1-C4 alcoholic solvent, and wherein the base used in step (a) is an alkali or an alkaline earth metal alkoxide selected from sodium methoxide, potassium tertiary butoxide, and sodium ethoxide.

14. The method of claim 10, wherein the polar aprotic solvent used in step (a) is dimethyl sulfoxide or dimethyl acetamide, optionally in combination with a C1-C4 alcoholic solvent, and the base used in step (a) is an alkali or alkaline carbonate.

15. The method of claim 14, wherein the alkaline carbonate used in step (a) is cesium carbonate.

* * * * *